(12) United States Patent
Chand et al.

(10) Patent No.: US 8,344,132 B2
(45) Date of Patent: Jan. 1, 2013

(54) METHODS FOR THE PREPARATION OF 9-DEAZAPURINE DERIVATIVES

(75) Inventors: Pooran Chand, Birmingham, AL (US); Minwan Wu, Vestavia Hills, AL (US); Pravin L. Kotian, Hoover, AL (US); V. Satish Kumar, Birmingham, AL (US); Tsu-Hsing Lin, Vestavia Hills, AL (US)

(73) Assignee: BioCryst Pharmaceticals, Inc., Birmingham, AL (US)

( * ) Notice: Subject to any disclaimer, the term of this patent is extended or adjusted under 35 U.S.C. 154(b) by 646 days.

(21) Appl. No.: 11/916,146

(22) PCT Filed: Jun. 21, 2006

(86) PCT No.: PCT/US2006/024134
§ 371 (c)(1),
(2), (4) Date: Dec. 8, 2009

(87) PCT Pub. No.: WO2007/002191
PCT Pub. Date: Jan. 4, 2007

(65) Prior Publication Data
US 2010/0093991 A1    Apr. 15, 2010

Related U.S. Application Data

(60) Provisional application No. 60/692,572, filed on Jun. 22, 2005.

(51) Int. Cl.
*C07H 21/00* (2006.01)
(52) U.S. Cl. .................. 536/25.3; 536/25.31; 536/25.33; 536/25.34

(58) Field of Classification Search .................. None
See application file for complete search history.

(56) References Cited

U.S. PATENT DOCUMENTS
4,584,369 A   4/1986   Klein et al.

FOREIGN PATENT DOCUMENTS
WO    WO 2006/050161   5/2006

OTHER PUBLICATIONS

Gaunt et al. J. Org. Chem. (1998), vol. 63, pp. 4172-4173.*
Tang et al. J. Org. Chem. (1999), vol. 64, pp. 747-754.*
International Search Report for International Application No. PCT/US06/24134 (2007).
Bhattacharya et al., *Nucleosides & Nucleotides*, 9(8), 1021-1043 (1986).
Bhattacharya et al., *Tetrahedron Letters*, 27(7), 815-818 (1986).
Chun et al., *J. Org., Chem.*, 66, 4852-4858 (2001).
Cupps et al., *J. Org. Chem.*, 51, 1058-1064 (1986).
Ingall et al., *J. Chem. Soc., Chem. Commun*, 83-84 (1994).
Lim et al., *J. Org. Chem.*, 48, 780-788 (1983).
Ren et al., *J. Org. Chem.*, 47, 4633-4637 (1982).
Tam et al., *J. Heterocyclic Chem.*, 13, 1305-1308 (1976).
Whistler et al., in *Methods Carbohydr. Chem.*, 2, 484-485 (1963).
Wu et al., *Synthesis*, 10, 1533-1553 (2004).

* cited by examiner

*Primary Examiner* — Patrick Lewis
(74) *Attorney, Agent, or Firm* — Dana M. Gordon; Foley Hoag LLP

(57) ABSTRACT

Methods for the preparation of the β isomer of a 9-deazapurine derivatives using benzyl protecting groups as the protecting groups for the 2 and 3 hydroxyl groups in ribose are provided.

6 Claims, No Drawings

METHODS FOR THE PREPARATION OF 9-DEAZAPURINE DERIVATIVES

CROSS-REFERENCE TO RELATED APPLICATIONS

This application is a National Stage application under 35 U.S.C. §371 of International Application No. PCT/US2006/024134, which has an International Filing Date of Jun. 21, 2006, which application is related to and claims priority under 35 U.S.C. §119(e) to U.S. Provisional Application No. 60/692,572 filed on Jun. 22, 2005, which applications are incorporated by reference herein.

TECHNICAL FIELD

The present disclosure relates to improved methods for the preparation of 9-deazapurine derivatives. The methods of the present disclosure make it possible to selectively obtain certain stereoisomers of the of 9-deazapurine derivatives. The methods of the present disclosure are relatively facile to carry out.

BACKGROUND ART

In nucleosides, at the position where the base (9-deazapurine in this case) is attached, two isomers (α and β) are possible and only β isomers of nucleosides have been found biologically active.

9-deazapurine derivatives represented by the following structural formula:

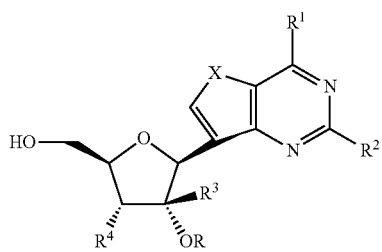

(I)

wherein:
X=NH, O, or S;
R=Benzyl, substituted benzyl such as 2,4-dichlorobenzyl, hydrogen, alkyl such as tert-butyl; or silyl such as tert-butyldimethylsilyl or tert-butyldiphenylsilyl;
$R^1$=H, OH, $NH_2$, Cl, $NR^5R^6$, alkyl, aryl, alkenyl, or alkynyl;
$R^2$=H, $NH_2$, $NHR^7$, or S-alkyl;
$R^3$=H, Alkyl, substituted alkyl, alkenyl, substituted alkenyl, alkynyl, or substituted alkynyl;
$R^4$=H, OH, $N_3$, or $NH_2$;
$R^5$ and $R^6$ independently are =H, alkyl, aryl, or both together with nitrogen can form a heterocyclic or substituted heterocyclic ring;
$R^7$=alkyl, acyl, or carbamate; and pharmaceutically acceptable salts thereof, are useful as antiviral and anticancer agents.

Various methods for the preparation of these 9-deazapurine derivatives have been described. For instance, methods for the preparation of compounds of structure I wherein R=H, $R^1$=OH, $NH_2$, $R^2$=$NH_2$, $R^3$=H, $R^4$=OH are described in following:

1. Klein et al. U.S. Pat. No. 4,584,369 (1986).
2. Bhattacharya et al. Nucleosides and Nucleotides 9(8), 1021-1043 (1986).
3. Bhattacharya et al. Tetrahedron letters 27(7), 815-818 (1986).
4. Ren et al. J. Org. Chem. 47, 4633-4637 (1982).
5. Tam et al. J. Heterocyclic Chem. 13, 1305-1308 (1976).
6. Lim et al. J. Org. Chem. 48, 780-788 (1983).
7. Chun et al. J. Org. Chem. 66, 4852-4858 (2001).
8. Cupps et al. J. Org. Chem. 51, 1058-1064 (1986).

All the above mentioned references have used isopropylidene group as a protecting group for 2- and 3-hydroxyl groups in ribose. When further reactions to prepare 9-deazapurine derivatives are carried out with this protecting group, it results in a mixture of α and β isomers in the approximate ratio of 1:2 to 1:1. In structure I when $R_3$=$CH_3$, and the isopropylidene group is used as the protecting group, the ratio of α and β is 9:1.

Accordingly, prior processes suffer from the inability to selectively produce the β isomer as the predominant isomer.

SUMMARY OF DISCLOSURE

The methods of the present disclosure overcome the above discussed problems of prior processes. The present invention makes it possible to selectively produce the β isomer as the predominant isomer.

The present invention provides a method for the preparation of the β isomer of a 9-deazapurine derivative, which comprises forming a 9-deazapurine base on a ribose protected with protecting groups at the 2- and 3-hydroxyl groups, and removing the protecting groups, wherein the protecting groups are benzyl groups.

The present disclosure provides methods for producing 9-deazapurine derivatives represented by the following structural formula:

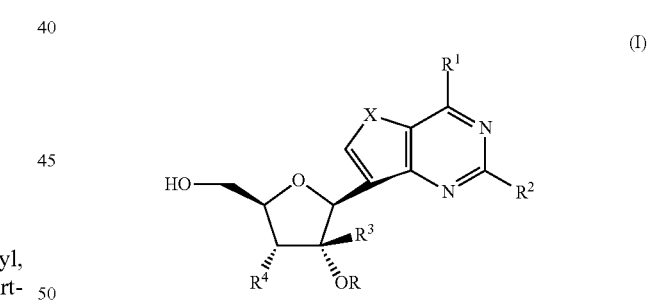

(I)

wherein:
X=NH, O, or S;
R=Benzyl, substituted benzyl such as 2,4-dichlorobenzyl, hydrogen, alkyl such as tert-butyl; or silyl such as tert-butyldimethylsilyl, tert-butyldiphenylsilyl;
$R^1$=H, OH, $NH_2$, Cl, $NR^5R^6$, alkyl, aryl, alkenyl, or alkynyl;
$R^2$=H, $NH_2$, $NHR^7$, or S-alkyl;
$R^3$=H, Alkyl, substituted alkyl, alkenyl, substituted alkenyl, alkynyl, or substituted alkynyl;
$R^4$=H, OH, $N_3$, or $NH_2$;
$R^5$ and $R^6$ independently are =H, alkyl, aryl, or both together with nitrogen can form a heterocyclic or substituted heterocyclic ring; and
$R^7$=alkyl, acyl, or carbamate; and pharmaceutically acceptable salts thereof, especially compounds of formula (I) in which R=hydrogen and $R_4$=OH.

According to the disclosure, benzyl is used as the protecting group for the 2 and 3 hydroxyl groups. By employing benzyl as the protecting group for the 2 and 3 hydroxyl groups, high ratios of the β isomer to the α isomer is obtainable. For instance, the use of the benzyl protecting group results in a ratio of α and β isomers of 1:19.

In addition, benzylation of ribonolactone or 2-C-methylribonolactone is not reported in the literature using benzyl bromide and sodium hydride as base. The use of these reagents makes the method very easy to carry out.

DESCRIPTION OF BEST AND VARIOUS EMBODIMENTS

In the method according to the invention, a 9-deazapurine base is formed on a ribose protected with benzyl protecting groups at the 2- and 3-hydroxyl groups. In one embodiment, the base is formed on ribose via an intermediate of formula (2-4) by a process that comprises the step of preparing a compound of formula (2-4):

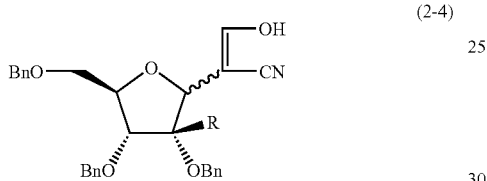

(2-4)

in which Bn represents a benzyl protecting group, and R represents a hydrogen atom or a methyl group from a compound of formula (1-3):

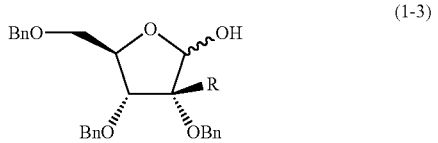

(1-3)

in which Bn represents a benzyl protecting group, and R represents a hydrogen atom or a methyl group.

The compounds of formulae (2-4) and (1-3) are believed to be novel, and are provided as further aspects of the invention.

One of aspect of the present disclosure is directed to a method for preparing (3R,4R,5R)-3,4-bis(benzyloxy)-5-(benzyloxymethyl)-dihydrofuran-2(3H)-one (1-2) and (3R,4R,5R)-3,4-bis(benzyloxy)-5-(benzyloxymethyl)-tetrahydrofuran-2-ol (1-3), which comprises (Scheme 1):

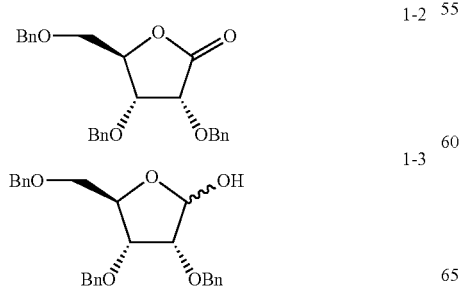

1-2

1-3

(a) contacting at least a stoichiometric equivalent of ribonolactone with sodium hydride and benzyl halide under conditions to effect benzylation to provide 1-2 (R=H);
(b) reducing the above lactone from (a) with suitable reducing agent, such as DIBAL or Red AL under conditions to effect reduction to provide 1-3 (R=H).

Another aspect of the present disclosure is directed to preparing (3R,4R,5R)-3,4-bis(benzyloxy)-5-(benzyloxymethyl)-3-methyl-dihydrofuran-2(3H)-one and (3R,4R,5R)-3,4-bis(benzyloxy)-5-(benzyloxymethyl)-3-methyl-tetrahydrofuran-2-ol under the same conditions given above.

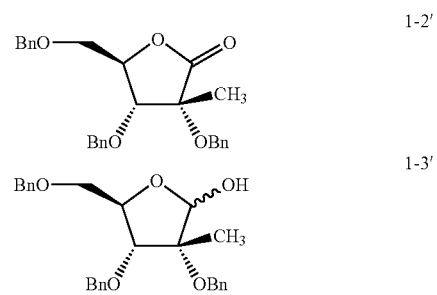

1-2'

1-3'

In another aspect, this disclosure is directed to a method for preparing (2S,3R,4S,5R)-2-(4-amino-5H-pyrrolo[3,2-d]pyrimidin-7-yl)-5-(hydroxymethyl)-tetrahydrofuran-3,4-diol (2-8) of the following formula, which comprises (Scheme 2):

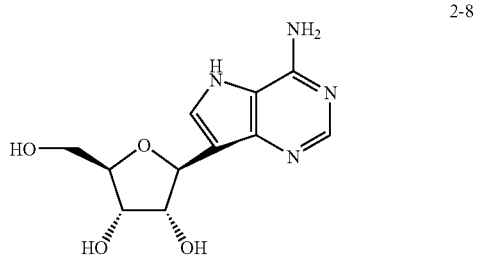 [SMILES: Nc1ncnc2c([C@@H]3O[C@H](CO)[C@@H](O)[C@H]3O)c[nH]c12]

2-8

(a) contacting at least a stoichiometric equivalent of 2-1 with base, such as sodium hydride or lithium hexamethyldisilazane and diethyl cyanomethylphosphonate under conditions to effect coupling to provide 2-2;
(b) reacting the above cyanomethyl derivative from (a) with at least a stoichiometric equivalent of Bredereck's reagent, tert-butoxy bis(dimethylamino)methane, under conditions to effect reaction to provide 2-3;
(c) hydrolyzing the dimethylamino group of compound from (b) with THF/acetic acid and water under conditions to be effective for hydrolysis to give 2-4;
(d) contacting the compound from (c) with at least stoichiometric equivalent of aminoacetonitrile hydrochloride in the presence of sodium acetate in a suitable solvent under conditions to effect coupling to provide 2-5;
(e) protecting the amino group of compound from (d) with at least stoichiometric equivalent of methyl chloroformate in the presence of a base, such as DBU and cyclizing the product with more base and then deprotecting the carbamate with a base such as sodium carbonate in a suitable solvent under conditions to provide 2-6;
(f) contacting the compound from (e) with at least a stoichiometric equivalent of formamidine acetate in a suitable solvent under conditions to effect reaction to provide 2-7;

(g) deprotecting the benzyl groups of the product from (f) by hydrogenation in the presence of a suitable catalyst, such as Pd/C or boron trichloride treatment under conditions to effect deprotection to provide 2-8.

Alternatively, compound 2-4 can be prepared directly from compound 2-2 by reaction with ethyl formate and sodium hydride.

This disclosure is also directed to preparing (2S,3R,4R,5R)-2-(4-amino-5H-pyrrolo[3,2-d]pyrimidin-7-yl)-5-(hydroxymethyl)-3-methyl-tetrahydrofuran-3,4-diol (2-8') under the same conditions given above.

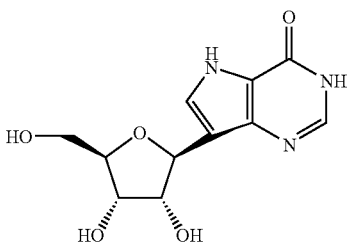

2-8'

In a further aspect, this disclosure is directed to a method for preparing 7-((2S,3R,4S,5R)-3,4-dihydroxy-5-(hydroxymethyl)-tetrahydrofuran-2-yl)-3H-pyrrolo[3,2-d]pyrimidin-4(5H)-one (3-4) of the following formula, which comprises (Scheme 3):

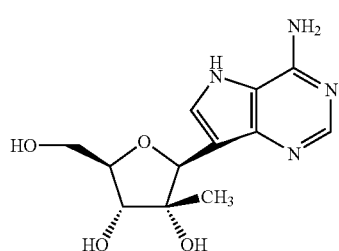

3-4

(a) contacting compound 2-4 with at least a stoichiometric equivalent of ethylglycinate hydrochloride in the presence of sodium acetate in a suitable solvent under conditions to effect coupling to provide 3-1;
(b) protecting the amino group of the compound from (a) with at least a stoichiometric equivalent of methyl chloroformate in the presence of a base, such as DBU and cyclizing the product with more base and then deprotecting carbamate with a base such as sodium carbonate in a suitable solvent under conditions to provide 3-2;
(c) contacting the compound from (b) with at least a stoichiometric equivalent of formamidine acetate in a suitable solvent under conditions to effect cyclization to provide 3-3;
(d) deprotecting the benzyl groups of the product from (c) by hydrogenation in the presence of a suitable catalyst, such as Pd/C or boron trichloride treatment under conditions to effect deprotection to provide 3-4.

This disclosure is also directed to prepare 7-((2S,3R,4R,5R)-3,4-dihydroxy-5-(hydroxymethyl)-3-methyl-tetrahydrofuran-2-yl)-3H-pyrrolo[3,2-d]pyrimidin-4(5H)-one (3-4') under the same conditions given above.

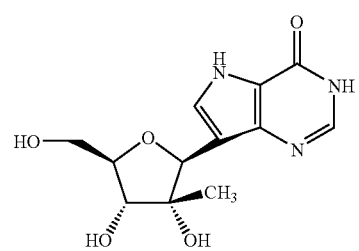

3-4'

In a still further aspect of the present disclosure a method is provided for preparing 2-amino-7-(2S,3R,4S,5R)-3,4-dihydroxy-5-(hydroxymethyl)-tetrahydrofuran-2-yl)-3H-pyrrolo[3,2-d]pyrimidin-4(5H)-one (3-7) the following formula, which comprises (Scheme 3):

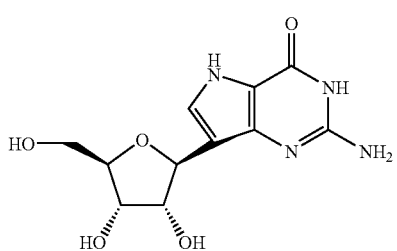

3-7

(a) contacting compound 3-2 with at least a stoichiometric equivalent of 1,3-bis(methoxycarbonyl)-2-methyl-2-thiopseudourea in the presence of a base such as triethylamine and mercury(II)chloride in a suitable solvent under conditions to effect coupling to provide 3-5;
(b) cyclization of the compound from (a) with at least a stoichiometric equivalent of a base such as sodium methoxide in methanol under conditions to provide 3-6;
(c) deprotecting the carbamate of the compound from (b) with a base such as sodium hydroxide and deprotecting the benzyl groups by hydrogenation in the presence of a suitable catalyst, such as Pd/C or boron trichloride treatment under conditions to effect deprotection to provide 3-7.

This disclosure is also directed to preparing 2-amino-7-(2S,3R,4R,5R)-3,4-dihydroxy-5-(hydroxymethyl)-3-methyl-tetrahydrofuran-2-yl)-3H-pyrrolo[3,2-d]pyrimidin-4(5H)-one (3-7') under the same conditions given above.

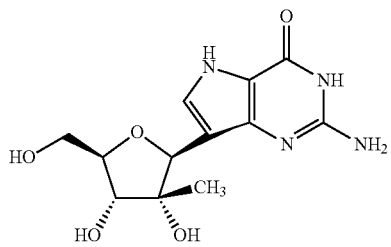

3-7'

In another aspect, this disclosure is directed to a method for preparing (2S,3R,4S,5R)-2-(4-aminothieno[3,2-d]pyrimidin-7-yl)-5-(hydroxymethyl)-tetrahydrofuran-3,4-diol (4-4) of the following formula, which comprises (Scheme 4):

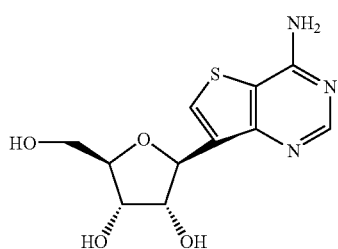

4-4

(a) contacting compound 2-4 with at least a stoichiometric equivalent of methanesulfonyl chloride in the presence of a base such as triethylamine in a suitable solvent under conditions to effect coupling to provide 4-1;
(b) displacement of the methanesulfonyl group of the compound from (a) with a thioacetonitrile group followed by cyclization through contacting with at least a stoichiometric equivalent of acetylthioacetonitrile in the presence of base, such as sodium carbonate in a suitable solvent under conditions to provide 4-2;
(c) contacting the compound from (b) with at least a stoichiometric equivalent of formamidine acetate in a suitable solvent under conditions to effect reaction to provide 4-3;
(d) deprotecting the benzyl groups of the product from (c) by hydrogenation in the presence of a suitable catalyst, such as Pd/C or boron trichloride treatment under conditions to effect deprotection to provide 4-4.

This disclosure is also directed to preparing (2S,3R,4R,5R)-2-(4-aminothieno[3,2-d]pyrimidin-7-yl)-5-(hydroxymethyl)-3-methyl-tetrahydrofuran-3,4-diol (4-4') under the same conditions given above.

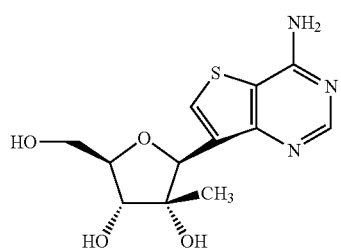

4-4'

In another of its aspects, this disclosure is directed to a method for preparing 7-(2S,3R,4S,5R)-3,4-dihydroxy-5-(hydroxymethyl)-tetrahydrofuran-2-yl)thieno[3,2-d]pyrimidin-4(3H)-one (5-3) of the following formula, which comprises (Scheme 5):

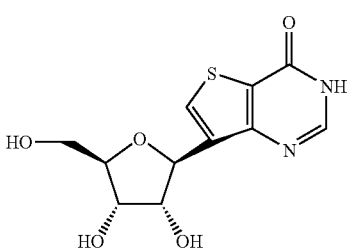

5-3

(a) displacement of the methanesulfonyl group of compound 4-1 with a thioacetamide group followed by cyclization through contacting with at least a stoichiometric equivalent of mercaptoacetamide in the presence of base, such as sodium carbonate in a suitable solvent under conditions to provide 5-1;
(b) contacting the compound from (a) with at least a stoichiometric equivalent of formamidine acetate in a suitable solvent under conditions to effect cyclization to provide 5-2;
(d) deprotecting the benzyl groups of the product from (b) by hydrogenation in the presence of a suitable catalyst, such as Pd/C or boron trichloride treatment under conditions to effect deprotection to provide 5-3.

This disclosure is also directed to preparing 7-(2S,3R,4R,5R)-3,4-dihydroxy-5-(hydroxymethyl)-3-methyl-tetrahydrofuran-2-yl)thieno[3,2-d]pyrimidin-4(3H)-one (5-3') under the same conditions given above.

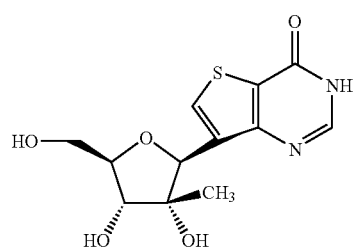

5-3'

In further aspect, this disclosure is directed to a method for preparing 2-amino-7-(2S,3R,4S,5R)-3,4-dihydroxy-5-(hydroxymethyl)-tetrahydrofuran-2-yl)thieno[3,2-d]pyrimidin-4(3H)-one (5-6) of the following formula, which comprises (Scheme 5):

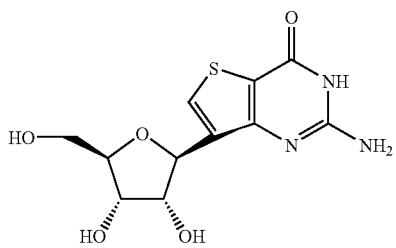

5-6

(a) contacting compound 5-1 with at least a stoichiometric equivalent of 1,3-bis(methoxycarbonyl)-2-methyl-2-thiopseudourea in the presence of a base such as triethylamine and mercury(II)chloride in a suitable solvent under conditions to effect coupling to provide 5-4;
(b) cyclization of the compound from (a) with at least a stoichiometric equivalent of a base such as sodium methoxide in methanol under conditions to provide 5-5;
(c) deprotecting the carbamate of the compound from (b) with a base such as sodium hydroxide and deprotecting the benzyl groups by hydrogenation in the presence of a suitable catalyst, such as Pd/C or boron trichloride treatment under conditions to effect deprotection to provide 5-6.

This disclosure is also directed to preparing 2-amino-7-(2S,3R,4R,5R)-3,4-dihydroxy-5-(hydroxymethyl)-3-methyl-tetrahydrofuran-2-yl)thieno[3,2-d]pyrimidin-4(3H)-one (5-6') under the same conditions given above.

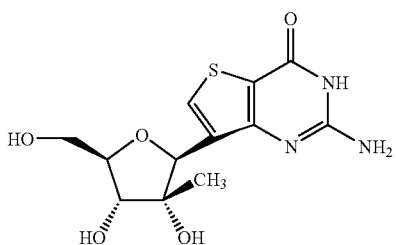

5-6'

In another of its aspects, this disclosure is directed to a method for preparing (2S,3R,4S,5R)-2-(4-aminofuro[3,2-d]pyrimidin-7-yl)-5-(hydroxymethyl)-tetrahydrofuran-3,4-diol (6-4) of the following formula, which comprises (Scheme 6):

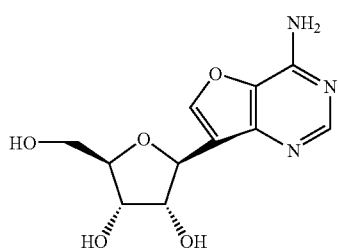

6-4

(a) contacting compound 2-4 with at least a stoichiometric equivalent of chloroacetonitrile in the presence of base, such as potassium fluoride and 18-crown-6 or sodium hydride in a suitable solvent under conditions to effect coupling to provide 6-1;
(b) cyclization of the compound from (a) through contacting with at least a stoichiometric equivalent of a base, such as lithium diisopropylamide in a suitable solvent under conditions to provide 6-2;
(c) contacting the compound from (b) with at least a stoichiometric equivalent of formamidine acetate in a suitable solvent under conditions to effect reaction to provide 6-3;
(d) deprotecting the benzyl groups of product from (c) by hydrogenation in the presence of a suitable catalyst, such as Pd/C or boron trichloride treatment under conditions to effect deprotection to provide 6-4.

This disclosure is also directed to preparing (2S,3R,4R,5R)-2-(4-aminofuro[3,2-d]pyrimidin-7-yl)-5-(hydroxymethyl)-3-methyl-tetrahydrofuran-3,4-diol (6-4') under the same conditions given above.

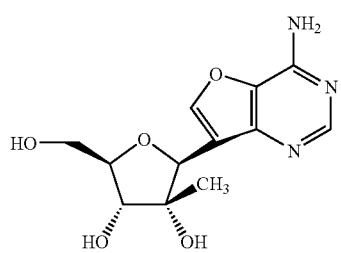

6-4'

The compound of formula 6-4' is of particular interest as an antiviral agent. It is described in WO 2006/050161, which was published after the priority date claimed for the present invention.

The compounds of formula (6-3) are believed to be novel, and are provided as a further aspect of the invention.

According to another aspect, the present invention provides a method for the preparation of (2S,3R,4S,5R)-2-(4-aminofuro[3,2-d]pyrimidin-7-yl)-5-(hydroxymethyl)-tetrahydrofuran-3,4-diol or (2S,3R,4R,5R)-2-(4-aminofuro[3,2-d]pyrimidin-7-yl)-5-(hydroxymethyl)-3-methyl-tetrahydrofuran-3,4-diol, or a pharmaceutically acceptable salt thereof, which comprises removing the benzyl protecting groups from a compound of formula (6-3).

In another of its aspects, this disclosure is directed to a method for preparing 7-(2S,3R,4S,5R)-3,4-dihydroxy-5-(hydroxymethyl)-tetrahydrofuran-2-yl)furo[3,2-d]pyrimidin-4(3H)-one (7-4) of the following formula, which comprises (Scheme 7):

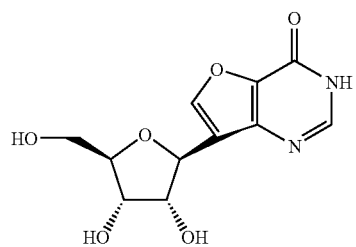

7-4

(a) contacting compound 2-4 with at least a stoichiometric equivalent of bromodiethylmalonate or bromoethylacetate in the presence of a base such as sodium hydride in a suitable solvent under conditions to effect coupling to provide 7-1;
(b) cyclization of the compound from (a) with at least a stoichiometric equivalent of a base, such as DBN in a suitable solvent under conditions to provide 7-2;
(c) contacting the compound from (b) with at least a stoichiometric equivalent of formamidine acetate in a suitable solvent under conditions to effect cyclization to provide 7-3;
(d) deprotecting the benzyl groups of the product from (c) by hydrogenation in the presence of a suitable catalyst, such as Pd/C or boron trichloride treatment under conditions to effect deprotection to provide 7-4.

This disclosure is also directed to preparing 7-(2S,3R,4R,5R)-3,4-dihydroxy-5-(hydroxymethyl)-3-methyl-tetrahydrofuran-2-yl)furo[3,2-d]pyrimidin-4(3H)-one (7-4') under the same conditions given above.

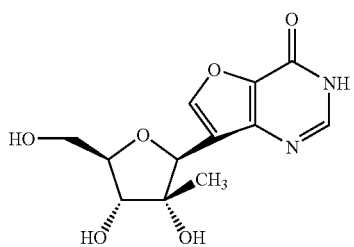

7-4'

In another of its aspects, this disclosure is directed to a method for preparing 2-amino-7-(2S,3R,4S,5R)-3,4-dihydroxy-5-(hydroxymethyl)-tetrahydrofuran-2-yl)furo[3,2-d]pyrimidin-4(3H)-one (7-7) of the following formula, which comprises (Scheme 7):

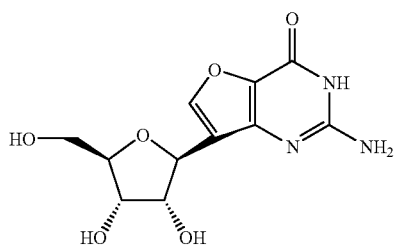

7-7

(a) contacting compound 7-2 with at least a stoichiometric equivalent of 1,3-bis(methoxycarbonyl)-2-methyl-2-thiopseudourea in the presence of a base such as triethylamine and mercury(II)chloride in a suitable solvent under conditions to effect coupling to provide 7-5;

(b) cyclization of the compound from (a) with at least a stoichiometric equivalent of a base such as sodium methoxide in methanol under conditions to provide 7-6;

(c) deprotecting the carbamate of the compound from (b) with a base such as sodium hydroxide and deprotecting the benzyl groups by hydrogenation in the presence of a suitable catalyst, such as Pd/C or boron trichloride treatment under conditions to effect deprotection to provide 7-7.

This disclosure is also directed to preparing 2-amino-7-((2S,3R,4R,5R)-3,4-dihydroxy-5-(hydroxymethyl)-3-methyl-tetrahydrofuran-2-yl)furo[3,2-d]pyrimidin-4(3H)-one (7-7') under the same conditions given above.

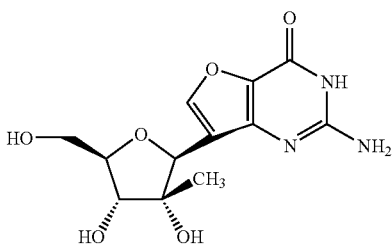

7-7'

Yet in another of its aspects, this disclosure is directed to an alternative method for preparing 2-6, 3-2, 4-2, 5-1, 6-2 and 7-2 according to Scheme 8. The method comprises (a) contacting compound 2-2 with at least a stoichiometric equivalent of ethylformate and a base such as sodium hydride in a suitable solvent under conditions to effect coupling to provide sodium salt 8-1;

(b) contacting compound 8-1 with at least a stoichiometric equivalent of aminoacetonitrile followed by protecting the amino group with methylchloroformate in the presence of a base such as DBU, cyclizing with more base and deprotecting the amino group with sodium carbonate in a suitable solvent under conditions to provide 2-6;

(c) contacting compound 8-1 with at least a stoichiometric equivalent of ethylglycinate followed by protecting the amino group with methylchloroformate in the presence of a base such as DBU, cyclizing with more base and deprotecting the amino group with sodium carbonate in a suitable solvent under conditions to provide 3-2;

(d) contacting compound 8-1 with at least a stoichiometric equivalent of acetylthioacetonitrile in the presence of a base such as sodium carbonate in a suitable solvent under conditions to provide 4-2;

(e) contacting compound 8-1 with at least a stoichiometric equivalent of mercaptoacetamide in the presence of a base such as sodium carbonate in a suitable solvent under conditions to provide 5-1;

(f) contacting compound 8-1 with at least a stoichiometric equivalent of bromoacetonitrile followed by cyclization with a base such as lithium diisopropylamide (LDA) in a suitable solvent under conditions to provide 6-2;

(g) contacting compound 8-1 with at least a stoichiometric equivalent of bromodiethylmalonate or bromoethylacetate followed by cyclization with a base such as DBN in a suitable solvent under conditions to provide 7-2;

In another of its aspects, this disclosure is directed to a method for preparing (2S,3R,4S,5R)-2-(4-aminopyrazolo[1,5-a][1,3,5]triazin-8-yl)-5-(hydroxymethyl)-tetrahydrofuran-3,4-diol (9-3) of the following formula, which comprises (Scheme 9):

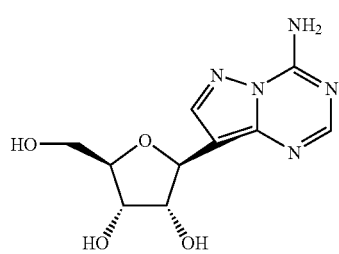

9-3

(a) contacting compound 2-3 with at least a stoichiometric equivalent of hydrazine and hydrazine hydrochloride in a suitable solvent under conditions to effect coupling and cyclization to provide 9-1;

(b) cyclization of the compound from (a) with at least a stoichiometric equivalent of N-cyanoethylformamidate in a suitable solvent under conditions to provide 9-2;

(c) deprotecting the benzyl groups of the product from (b) by hydrogenation in the presence of a suitable catalyst, such as Pd/C or boron trichloride treatment under conditions to effect deprotection to provide 9-3.

This disclosure is also directed to preparing (2S,3R,4R,5R)-2-(4-aminopyrazolo[1,5-a][1,3,5]triazin-8-yl)-5-(hydroxymethyl)-3-methyl-tetrahydrofuran-3,4-diol (9-3') under the same conditions given above.

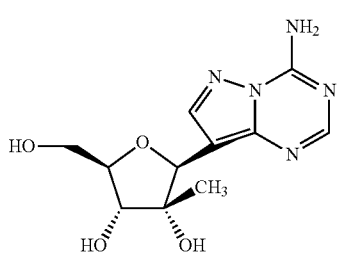

9-3'

Definition of Terms

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms. Alkyl groups may be substituted with halo (Cl, F, Br, I), OH, etc.

The terms "alkenyl" and "alkynyl" refer to straight or branched chain unsubstituted hydrocarbon groups typically having 2 to 8 carbon atoms.

The terms "substituted alkyl", "substituted alkenyl" or substituted alkynyl" refer to an alkyl, alkenyl or alkynyl group substituted by, for example, one to four substituents, such as halo, trifluoromethyl, trifluoromethoxy, hydroxy, alkoxy, cycloalkyloxy, heterocyclooxy, oxo, alkanoyl, aryloxy, alkanoyloxy, amino, allylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanolamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above, where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "acyl" refers to the residual moiety of a carboxylic acid group without the OH group of the acid and includes alkyl and acyl carboxylic acids. The alkyl group typically contains about 1-20 carbon atoms and more typically about 1-8 carbon atoms. The acyl group typically contains 2-12 carbon atoms. Examples of suitable acyl groups include acetyl and benzoyl.

The term "benzyl protecting group" refers to any benzyl protecting group capable of functioning as a protecting group for the 2- and 3-hydroxyl groups during the preparation of the β isomer of a 9-deazapurine derivative. Benzyl protecting groups are well known in the art.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Within the above-described definitions, certain embodiments are preferred. Preferred alkyl groups are lower alkyl groups containing 1 to about 8 carbon atoms, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. The aromatic or aryl groups are preferably phenyl and alkyl substituted aromatic groups (aralkyl) such as phenyl $C_{1-3}$ alkyl and benzyl.

In one embodiment of the invention $R^3$=Alkyl, substituted alkyl, alkenyl, substituted alkenyl, alkynyl, or substituted alkynyl.

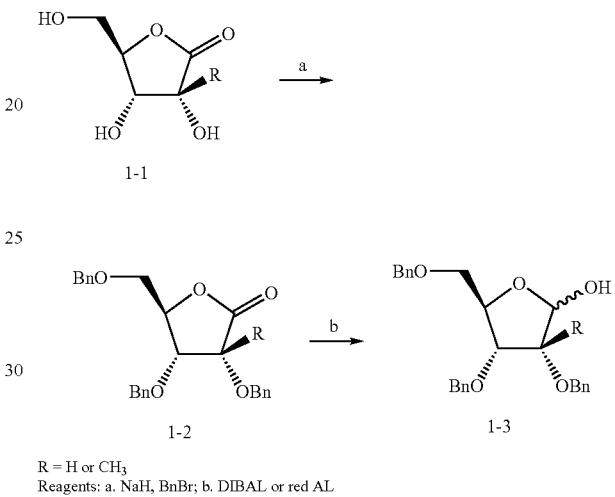

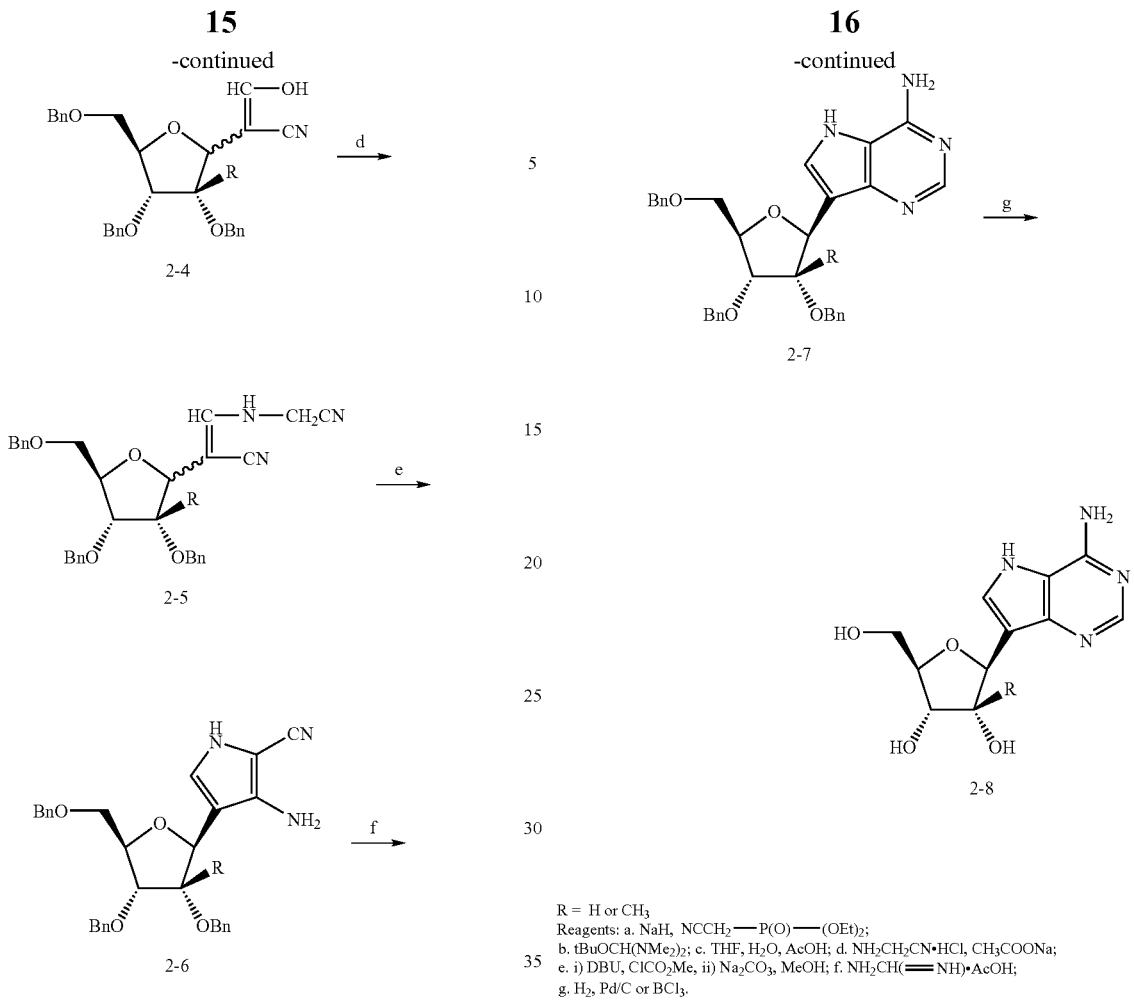
R = H or CH3
Reagents: a. NaH, NCCH2—P(O)—(OEt)2;
b. tBuOCH(NMe2)2; c. THF, H2O, AcOH; d. NH2CH2CN·HCl, CH3COONa;
e. i) DBU, ClCO2Me, ii) Na2CO3, MeOH; f. NH2CH(=NH)·AcOH;
g. H2, Pd/C or BCl3.
Scheme 3.
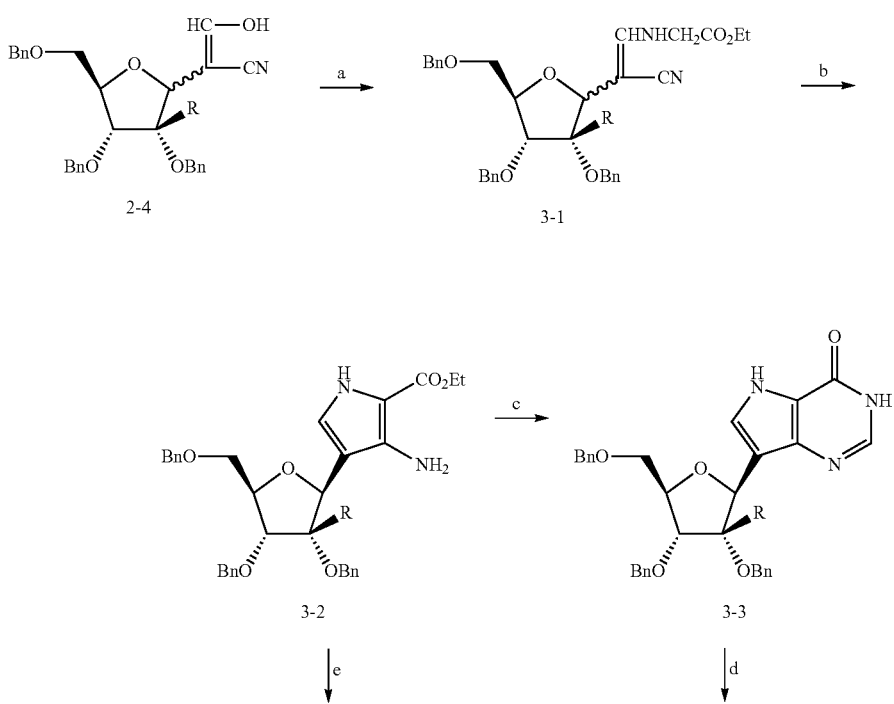

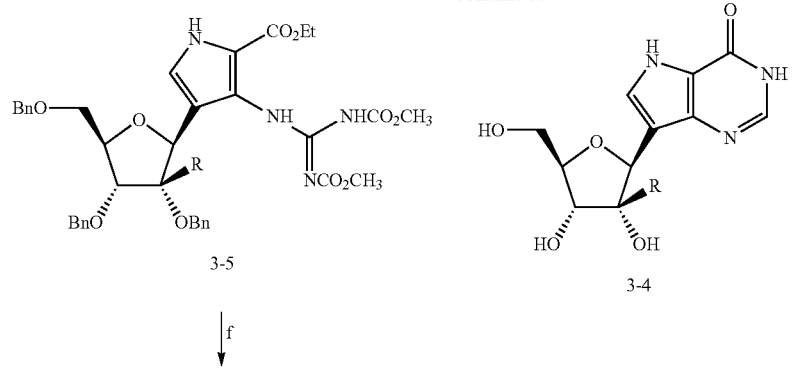
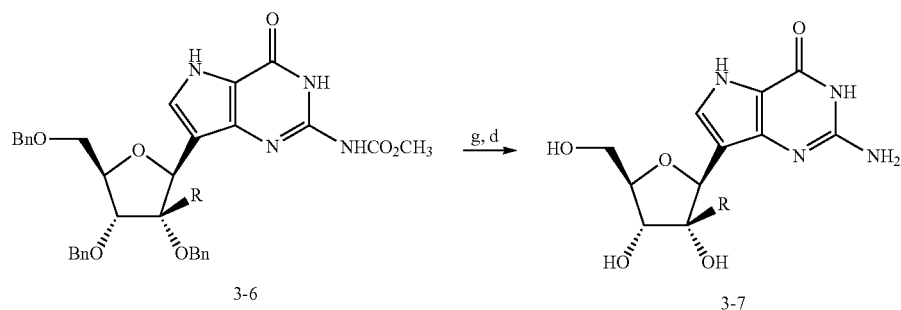
R = H or CH₃
Reagents: a. H₂NCH₂CO₂Et·HCl, CH₃CO₂Na; b. i) ClCO₂Me, DBU; ii) Na₂CO₃, MeOH; c. H₂NCH(=NH)·AcOH; d. H₂, Pd/C or BCl₃; e. H₃CS—C(=NHCO₂Me)NHCO₂Me, HgCl₂, Et₃N; f. NaOMe, MeOH; g. NaOH.
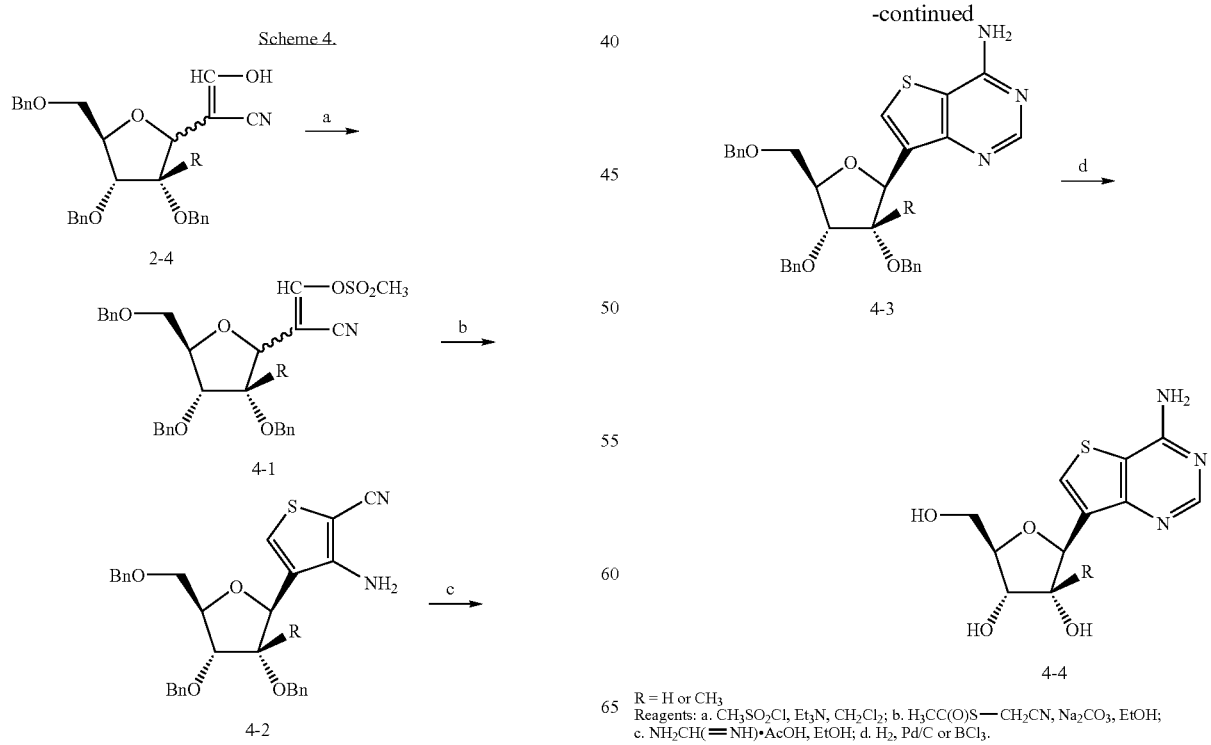
R = H or CH₃
Reagents: a. CH₃SO₂Cl, Et₃N, CH₂Cl₂; b. H₃CC(O)S—CH₂CN, Na₂CO₃, EtOH; c. NH₂CH(=NH)·AcOH, EtOH; d. H₂, Pd/C or BCl₃.

Scheme 5.
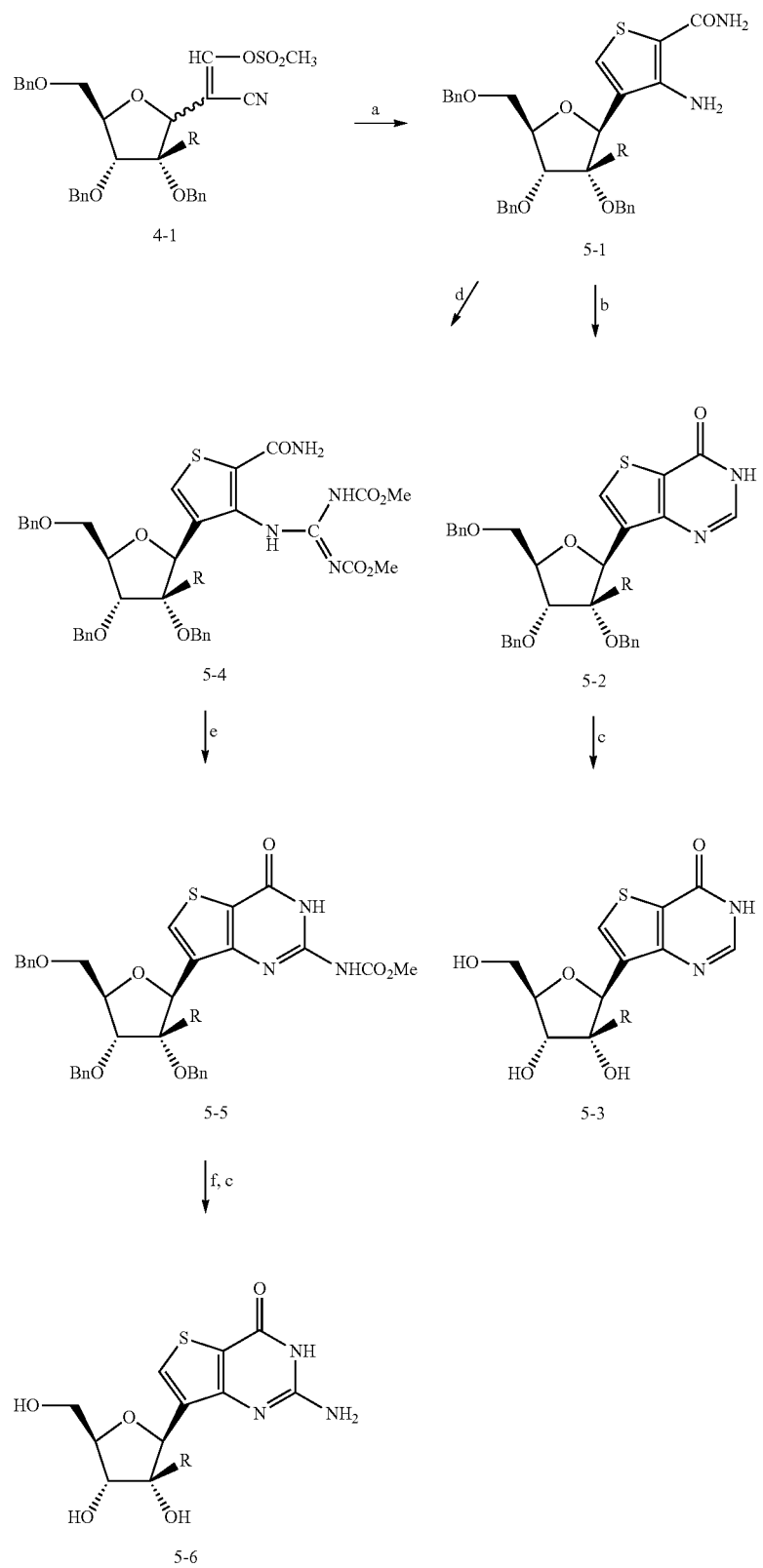
R = H or CH₃
Reagents: a. Mercaptoacetamide, EtOH, Na₂CO₃; b. (EtO)₃CH; c. H₂, Pd/C or BCl₃;
d. H₃CS—C(=NHCO₂Me), NHCO₂Me, HgCl₂, Et₃N; e. NaOMe, MeOH; f. NaOH.

21 22
Scheme 6.
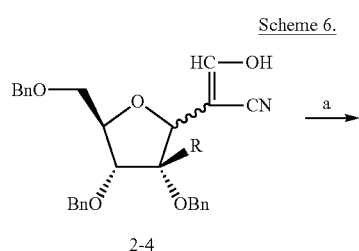
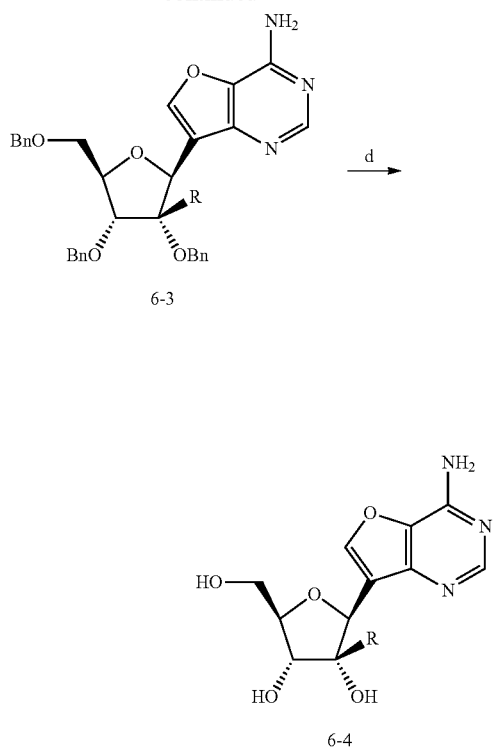
R = H or CH₃
Reagents: a. ClCH₂CN, KF, 18-crown-6, DMF; b. LDA, THF;
c. CH(=NH)NH₂·AcOH, EtOH; d. H₂, Pd/C or BCl₃.
Scheme 7.
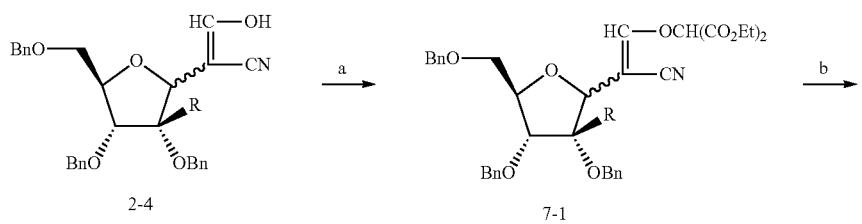
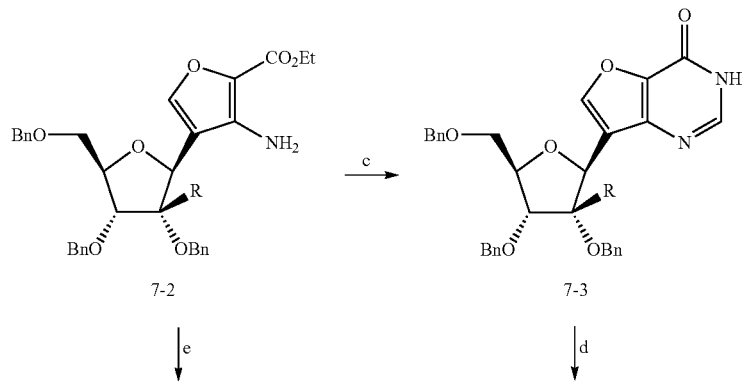

-continued
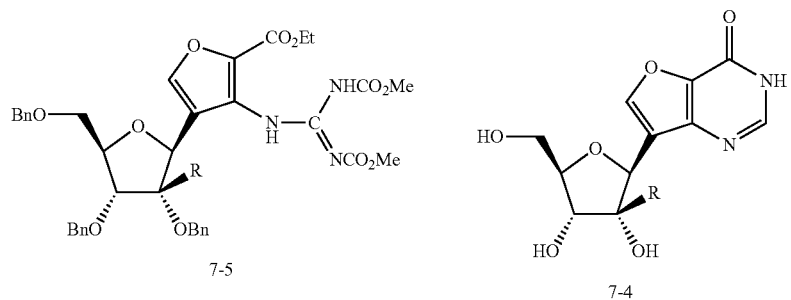
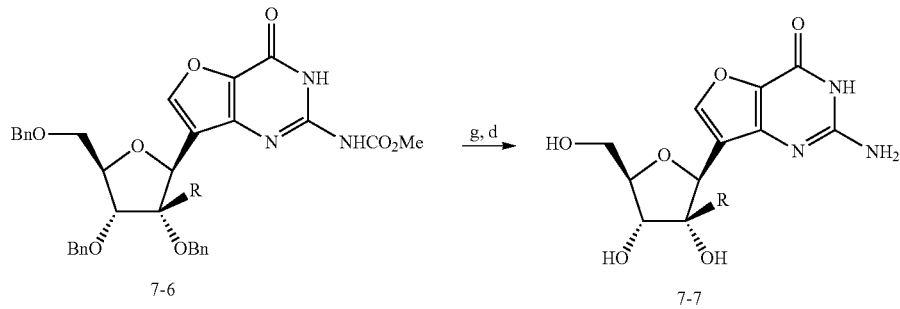
R = H or CH₃
Reagents: a. NaH, bromodiethylmalonate; b. DBN, EtOH; c. H₂NCH(=NH)·AcOH;
d. H₂, Pd/C or BCl₃; e. H₃CS—C(=NHCO₂Me)NHCO₂Me, HgCl₂, Et₃N; f. NaOMe, MeOH; g. NaOH.
Scheme 8.
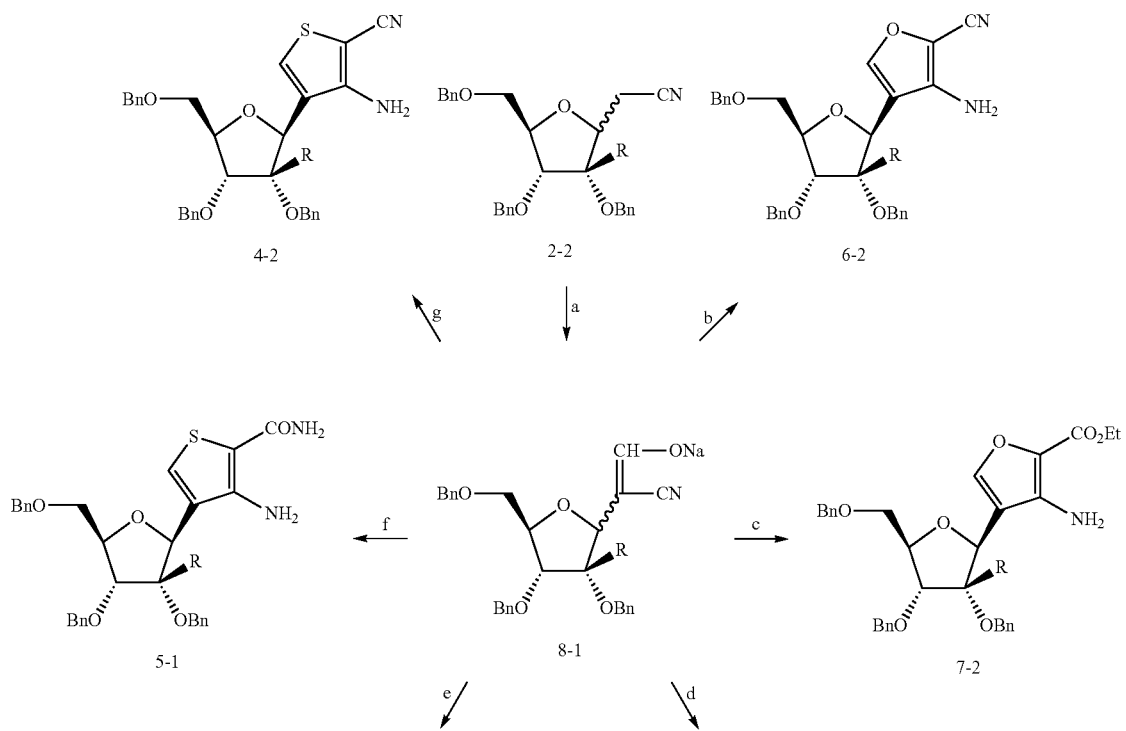

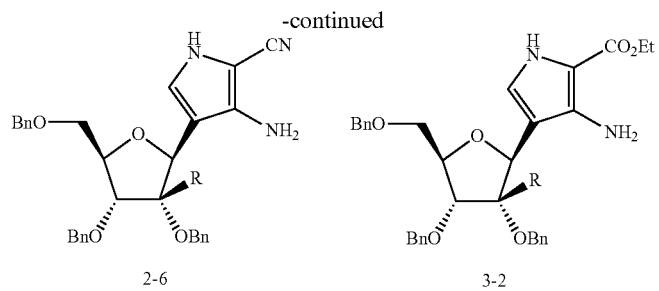

2-6          3-2

R = H or CH$_3$

Reagents: a. NaH, ethyl formate; b. i) BrCH$_2$CN; ii) LDA; c. i) BrCH(CO$_2$Et)$_2$; ii) DBN, EtOH; d. i) NH$_2$·CH$_2$·CO$_2$Et; ii) ClCO$_2$Me, DBU; e. i) H$_2$NCH$_2$CN; ii) ClCO$_2$Me, DBU; f. Mercaptoacetamide, Na$_2$CO$_3$, EtOH; g. CH$_3$C(O)S—CH$_2$CN, Na$_2$CO$_3$, EtOH.

Scheme 9.

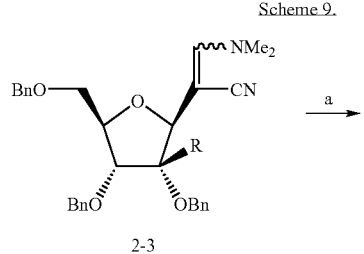

2-3

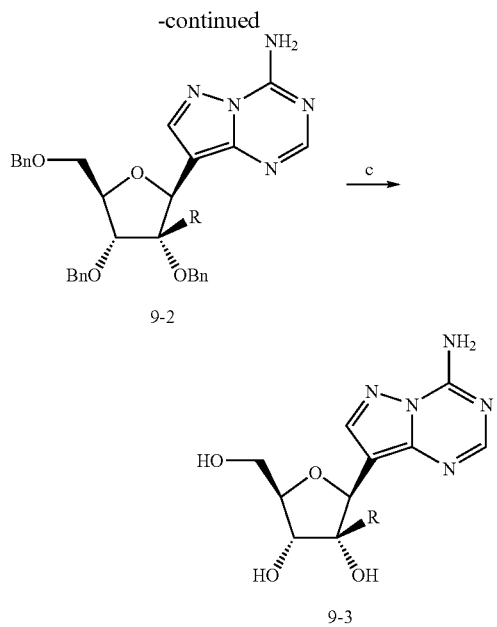

9-2

9-3

R = H or CH$_3$
Reagents: NH$_2$—NH$_2$, NH$_2$—NH$_2$·HCl, MeOH; b. NC—N=CH—OEt; c. H$_2$, Pd/C or BCl$_3$.

9-1

The following example illustrates the invention.

EXAMPLE 1

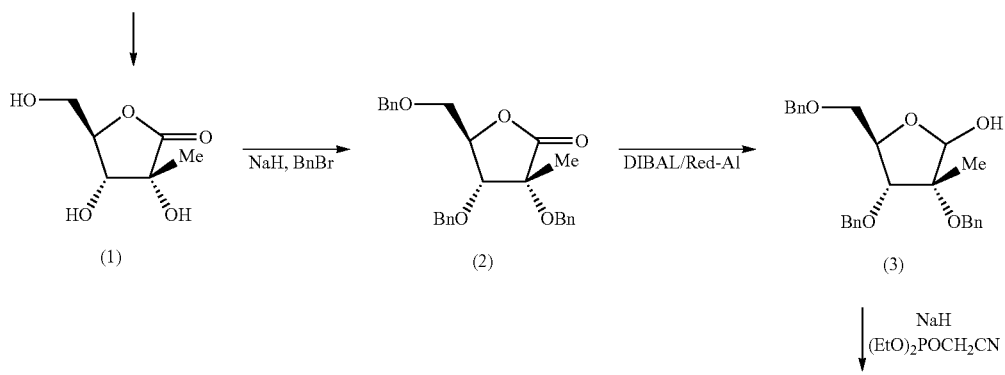

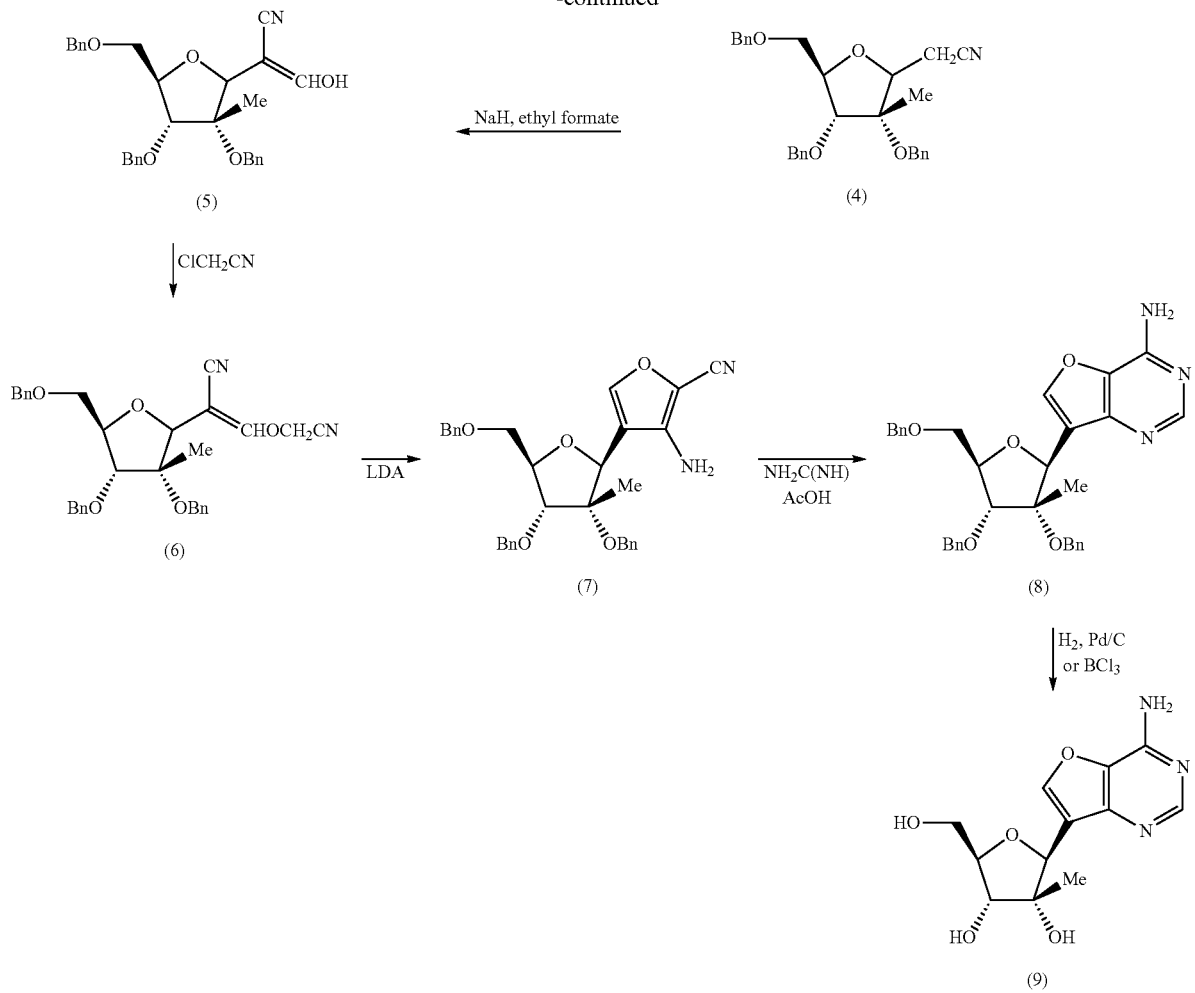

3,4-Dihydroxy-5-hydroxymethyl-3-methyl-dihydro-furan-2-one (1): D-fructose was converted to 3,4-dihydroxy-5-hydroxymethyl-3-methyl-dihydro-furan-2-one by slight modification of the method reported by Whistler et al. in Methods Carbohydr. Chem., 1963, 12, 484-485.

(3R,4R,5R)-3,4-Bis(benzyloxy)-5-(benzyloxymethyl)-3-methyl-dihydrofuran-2(3H)-one (2)

To sodium hydride (8.75 Kg, 218.75 moles, 60% in mineral oil) in DMF (100 L) under nitrogen atmosphere was added drop-wise, 3,4-dihydroxy-5-hydroxymethyl-3-methyl-dihydro-furan-2-one (10.13 kg, 62.5 moles) in DMF (40 L) at the rate maintaining internal temperature between 5° C.-10° C. The reaction was stirred at 5° C.-10° C. for 15 mins and allowed to warm to RT and maintained at RT for 2 h. After cooling the reaction mixture to about 5° C., benzyl bromide (33 L, 277.44 moles) was added maintaining internal temperature between 5-10° C. The reaction mixture was stirred between 5-10° C. for additional 30 mins and brought to RT and stirred for 3 h. TLC analysis showed the completion of reaction (25% ethyl acetate in hexanes). The mixture was quenched carefully with water (100 L) and was extracted twice with toluene (75 L, 50 L). The toluene layers were combined, washed with water (50 L) and brine (2×30 L), dried over anhydrous Magnesium sulfate (25 Kg) and filtered.

The filtrate was used as such for next step. A small amount of filtrate was concentrated in vacuum and purified by flash column chromatography (silica gel, ethyl acetate in hexane) to furnish a pure analytical sample of the product. $^1$H NMR (DMSO-$d_6$): δ 7.36-7.27 (m, 15 H), 4.75 (d, J=11.5 Hz, 1 H), 4.61 (d, J=11.5 Hz, 1 H), 4.59-4.47 (m, 6 H), 4.09 (d, J=7.5 Hz, 1 H), 3.75 (dd, J=11.7, 2.5 Hz, 1 H), 3.61 (dd, J=11, 5, 5 Hz, 1H), 1.52 (s, 3 H); MS (ES$^+$): 455.18 (M+Na). [α]=+99.10 [c 1.34, CHCl$_3$].

Analysis: Calculated for $C_{27}H_{28}O_5$: C, 74.98; H, 6.53; Found: C, 75.10; H, 6.55.

(3R,4R,5R)-3,4-Bis(benzyloxy)-5-(benzyloxymethyl)-3-methyl-tetrahydrofuran-2-ol (3): Vitride (22 L, 76.19 mole, 70% wt. in toluene, 3.46M) was diluted with toluene (18 L) and added dropwise to a solution of (3R,4R,5R)-3,4-bis(benzyloxy)-5-(benzyloxymethyl)-3-methyl-dihydrofuran-2 (3H)-one (62.5 mole from step 1) in toluene (150 L) maintaining temperature around −40±5° C. during the addition. After the addition was over, TLC was checked to ensure completion of the reaction (if the reaction is not complete, more Vitride is added till reaction is complete). The reaction was quenched with acetone (5.5 L) maintaining temperature between −30° C. and −40° C. and 2.5 N HCl (70 L) was added at 0° C. The toluene layer was separated and the aqueous layer was extracted with ethyl acetate (30 L). The combined organic layers were washed with brine (30 L), dried over magnesium sulfate (10 Kg), filtered and the filtrate was concentrated in vacuo to dryness to furnish 32 kg of crude residue. The crude material was used as such for the next step. An analytical sample was prepared by purification of 1 g of residue by flash column chromatography (silica gel, ethyl acetate in hexane) to furnish (3R,4R,5R)-3,4-bis(benzyloxy)-5-(benzyloxymethyl)-3-methyl-tetrahydrofuran-2-ol.
$^1$HNMR (DMSO-d$_6$): δ 7.35-7.24 (m, 15 H), 6.68 (d, J=5 Hz, 0.6 H), 5.89 (d, J=6.8 Hz, 0.4 H), 5.00 (m, 1 H), 4.73-4.50 (m, 6 H), 4.18-4.13 (m, 0.4 H), 4.06-4.00 (m, 0.6 H), 3.79 (d, J=7.5 Hz, 0.6 H), 3.65 (d, J=6 Hz, 0.4 H), 3.61-3.48 (m, 2 H), 1.33 (s, 2 H), 1.32 (s, 1 H); MS (ES$^+$): 457.38 (100% M+Na). Analysis: Calculated for $C_{27}H_{30}O_5$: C, 74.62; H, 6.96; Found: C, 74.36; H, 7.05.

Alternatively, Compound 3 can be Prepared Using Diisobutylaluminum Hydride (Dibal):

To a solution of (3R,4R,5R)-3,4-Bis(benzyloxy)-5-(benzyloxymethyl)-3-methyl-dihydrofuran-2(3H)-one (250 mmol) in toluene (625 mL) cooled to −70° C. was added dropwise a 1.5 M solution of Dibal in Toluene (250 mL, 375 mmol) at such a rate so that the reaction temperature does not go above −65° C. The reaction was further stirred at −65° C. for 15 mins (TLC analysis showed completion of reaction, 25% ethyl acetate in hexanes). The excess Dibal was destroyed by adding acetone (40 mL) to the reaction mixture while maintaining the temperature below −60° C. The reaction was diluted with cold 2.5 N HCl (300 mL), water (475 mL) and allowed to warm to 0° C. The reaction was extracted with ethyl acetate (625 mL). The organic layer was separated and washed with brine (500 mL), dried over MgSO4, filtered and the filtrate was concentrated in vacuum to dryness to furnish (3R,4R,5R)-3,4-bis(benzyloxy)-5-(benzyloxymethyl)-3-methyl-tetrahydrofuran-2-ol (112 g) as an oil, which was used in the next step without further purification.

2-(3S,4R,5R)-3,4-Bis(benzyloxy)-5-(benzyloxymethyl)-3-methyl-tetrahydrofuran-2-yl)acetonitrile (4); To a slurry of sodium hydride (2.8 Kg, 70 moles) in DME (60 L) at 0-5° C. was added diethylcyanomethyl phosphonate (11 L, 68 moles) at a rate maintaining reaction temperature at 5±5° C. The heterogeneous mixture became homogenous after stirring for 30 mins at 0-5° C. To this mixture was added, a solution of product from above step, (3R,4R,5R)-3,4-bis(benzyloxy)-5-(benzyloxymethyl)-3-methyl-tetrahydrofuran-2-ol, in DME (15 L) dropwise at 5±5° C. and the mixture was allowed to warm to room temperature overnight (TLC analysis showed completion of reaction, 25% ethyl acetate in hexanes). The reaction was quenched with water (50 L) and extracted with ethyl acetate (30 L, 10 L). The organic layers were combined and washed with brine (30 L), dried over MgSO$_4$ (10 Kg), filtered and the filtrate was concentrated in vacuum to dryness to furnish 32.7 Kg crude 2-(3S,4R,5R)-3,4-bis(benzyloxy)-5-(benzyloxymethyl)-3-methyl-tetrahydrofuran-2-yl)acetonitrile as an oil, which was used without further purification. An analytical sample was prepared by purification of 1 g of residue by flash column chromatography (silica gel, ethyl acetate in hexane): $^1$HNMR (DMSO-d$_6$): δ 7.37-7.28 (m, 15 H), 4.82 (d, J=11.5 Hz, 0.6 H), 4.67-4.47 (m, 0.4 H), 4.14-4.04 (m, 1 H), 191 (d, J=7 Hz, 0.6 H), 3.79 (d, J=5.5 Hz, 0.4 H), 3.63-3.56 (m, 2 H), 2.85-2.67 (m, 2H), 1.42 (s, 2 H), 1.28 (s, 1 H).

2-(3S,4R,5R)-3,4-Bis(benzyloxy)-5-(benzyloxymethyl)-3-methyl-tetrahydrofuran-2-yl)-3-(cyanomethoxy)acrylonitrile (6): To a solution of 2-((3S,4R,5R)-3,4-bis(benzyloxy)-5-(benzyloxymethyl)-3-methyl-tetrahydrofuran-2-yl) acetonitrile (62.5 mole crude) from above step in DMF (60 L) cooled to 10±5° C. was added sodium hydride (7.74 Kg, 194 mole, 60% in mineral oil) over a period of 1 h in four installments maintaining inside temperature at 15±5° C. during addition. The reaction mixture was brought to RT and was stirred for 1 h and again cooled to 10±5° C. To this cold solution, was added ethyl formate (15 L, 186.5 mole), slowly to control evolution of gases. After addition, the reaction mixture was stirred at RT for 16 h (TLC analysis showed completion of reaction, 25% ethyl acetate in hexanes). The reaction mixture was again cooled to 10±5° C. and chloroacetonitrile (15.75 L, 250 mol) was added over a period of 1 h and the mixture was warmed to RT and stirred for 48 h. After the reaction was complete (checked by TLC), the mixture was quenched carefully with water (150 L) and left for 24 h. Upper aqueous layer was decanted and washed with 10% toluene in hexanes (80 L) to remove impurities and then aqueous layer was extracted with toluene (60 L). The toluene extract was added to the lower oily layer, organic layer was separated and washed with water (50 L), brine (30 L) and dried over MgSO$_4$ (10 Kg). After filtration, the filtrate was concentrated in vacuum to dryness to furnish 31 kg of crude (E)-2-(2S,3S,4R,5R)-3,4-bis(benzyloxy)-5-(benzyloxymethyl)-3-methyl-tetrahydrofuran-2-yl)-3-(cyanomethoxy)acrylonitrile as an oil, which was used without further purification. This product can be purified by flash column chromatography (silica gel 0-30% ethyl acetate in hexanes) prior to use in the next step to reduce the amounts of solvent and reagents. The required product is the least polar of the four isomers. An analytical sample was prepared by column chromatography on silica gel using hexanes/ethyl acetate. $^1$H NMR (DMSO-d$_6$): δ 7.56 (s, 1 H), 7.37-7.27 (m, 15 H), 5.12 (s, 2 H), 4.60-4.54 (m, 6 H), 4.41 (s, 1 H), 4.12-4.08 (m, 1 H), 3.77 (d, J=5.65 Hz, 1H), 3.67-3.56 (m, 2 H), 1.31 (s, 3 H); MS (ES$^+$): 525.40 (M+1). Analysis: Calculated for $C_{32}H_{32}N_2O_5$: C, 73.26; H, 6.15; N, 5.34; Found: C, 73.36; H, 6.16; N, 5.45.

3-Amino-4-(2S,3S,4R,5R)-3,4-bis(benzyloxy)-5-(benzyloxymethyl)-3-methyl-tetrahydrofuran-2-yl)furan-2-carbonitrile (7): To a solution of diisopropyl amine (1.62 L, 11.45 mol) in THF (9.3 L) was added a solution of n-BuLi (2.6 M solution in hexane, 4.39 L, 11.45 mol) dropwise at 0° C. and stirred further at 0° C. for 30 mins and cooled to −70° C. To this solution of LDA formed was added a solution of product from previous step, 2-((3S,4R,5R)-3,4-bis(benzyloxy)-5-(benzyloxymethyl)-3-methyl-tetrahydrofuran-2-yl)-3-(cyanomethoxy)acrylonitrile (crude 2 Kg, 3.82 mole) in THF (2.9 L) dropwise maintaining the temperature below −65° C. TLC analysis of the reaction mixture in 25% ethyl acetate in hexanes showed completion of reaction after 15 mins. The reaction mixture was quenched with 2.5 N HCl (9 L, pH=6). The organic layer was separated and aqueous layer was extracted with ethyl acetate (6 L).

The organic layers were combined and washed with brine (5 L), dried over MgSO$_4$, filtered and the filtrate was concentrated in vacuum to dryness to furnish 2 Kg crude product as dark brown oil. A total of 31 Kg material from the previous step was processed the same way. All combined batches of crude product were purified by flash column chromatography (silica gel, eluting with 0-30% ethyl acetate in hexanes) to furnish 3-amino-4-(2S,3S,4R,5R)-3,4-bis(benzyloxy)-5-(benzyloxymethyl)-3-methyl-tetrahydrofuran-2-yl)furan-2-carbonitrile as a yellow oil (12.6% yield in 5 steps). $^1$HNMR (DMSO-d$_6$): δ 7.52 (d, J=0.94 Hz, 1H), 7.38-7.26 (m, 15 H), 5.63 (bs, 2H, D$_2$O exchangeable), 4.83 (d, J=0.94 Hz, 1H), 4.62-4.54 (m, 6H), 4.17 (q, J=4.71 Hz, 1H), 3.89 (d, J=4.89 Hz, 1H), 3.69-3.59 (m, 2H), 1.15 (s, 3H); MS (ES$^+$): 547.33 (100% M+Na), (ES$^-$): 523.24 (M$^{-1}$). [α]=−49.72 [c 0.535, CHCl$_3$]. Analysis: Calculated for $C_{32}H_{32}N_2O_5$: C, 73.26; H, 6.14; N, 5.33; Found: C, 73.67; H, 6.33; N, 4.90.

7-(2S,3S,4R,5R)-3,4-Bis(benzyloxy)-5-(benzyloxymethyl)-3-methyl-tetrahydrofuran-2-yl)furo[3,2-d]pyrimidin-4-amine (8): To the product from above step, 3-amino-4-(2S, 3S,4R,5R)-3,4-bis(benzyloxy)-5-(benzyloxymethyl)-3-methyl-tetrahydrofuran-2-yl)furan-2-carbonitrile (2.1 kg, 4.03 mole) in ethanol (13 L) was added powdered formamidine acetate (4.19 Kg, 40.3 mole). The reaction mixture was heated at reflux for 24 h and additional formamidine acetate (2.1 Kg, 20 moles) was added. The reaction mixture was further heated at reflux for additional 60 h. TLC analysis in 25% ethyl acetate in hexanes showed all starting material is consumed. The reaction mixture was cooled to RT and excess formamidine acetate was removed by filtration. The filtrate was concentrated in vacuo and dissolved in ethyl acetate (10 L). The ethyl acetate layer was washed with water (5 L) and concentrated in vacuo to give crude residue which was purified by flash column chromatography (silica gel, eluting with 0-50% ethyl acetate in hexanes followed by 0-50% of 10% methanol in ethyl acetate diluted with hexanes) to furnish 2.05 Kg (92%) of the desired product, 7-(2S,3S,4R,5R)-3,4-bis(benzyloxy)-5-(benzyloxymethyl)-3-methyl-tetrahydrofuran-2-yl)furo[3,2-d]pyrimidin-4-amine as an oil. $^1$H NMR (DMSO-d$_6$): δ 8.26 (s, 1 H), 8.12 (s, 1 H), 7.39-7.25 (m, 17 H), 5.25 (s, 1 H), 4.77-4.52 (m, 6 H), 4.22-4.14 (m, 2 H), 3.78 (dd, J=2.7 and 11 Hz, 1 H), 3.72 (dd, 11 and 4.5 Hz, 1 H), 1.21 (s, 3 H); MS (ES): 552.31 (M+1). Analysis: Calculated for $C_{33}H_{33}N_3O_5.H_2O$: C, 69.55; H, 6.20; N, 7.38; Found: C, 69.59; H, 6.22; N, 7.29.

(2S,3R,4R,5R)-2-(4-Aminofuro[3,2-d]pyrimidin-7-yl)-5-(hydroxymethyl)-3-methyl-tetrahydrofuran-3,4-diol (9): To a solution of 7-(2S,3S,4R,5R)-3,4-bis(benzyloxy)-5-(benzyloxymethyl)-3-methyl tetrahydrofuran-2-yl)furo[3,2-d]pyrimidin-4-amine (2.05 Kg, 3.72 mole) in dichloromethane (9.5 L) cooled to 5±5° C. was added dropwise, a solution of BCl$_3$ (18.6 L, 18.6 mole, 1 M solution in dichloromethane). The addition rate was controlled to maintain internal temperature at 5±5° C. and the slurry obtained was stirred at that temperature for 30 mins after the addition of BCl$_3$ was over. The reaction was cautiously quenched with ethanol (5.4 L) maintaining internal temperature at 10±5° C. The homogenous solution was diluted with water (1 L) and stirred at room temperature for minimum of 3 h. The solid obtained was collected by filtration, washed with ethyl acetate (3 L) and air dried overnight to give 2.06 Kg of borate complex of (2S,3R,4R,5R)-2-(4-aminofuro[3,2-d]pyrimidin-7-yl)-5-(hydroxymethyl)-3-methyl-tetrahydrofuran-3,4-diol as a light brown solid. To the borate complex was added ethanol (16 L) and conc. HCl (3.25 L) and the solution was heated at gentle reflux for 1 h. The solution was cooled to room temperature and concentrated in vacuo to remove ethanol and excess HCl. To the residue obtained was added ethanol (13.75 L) and water (1.375 L), heated until a homogenous solution was obtained and heating was continued further at gentle reflux for additional 1 h. The solution was cooled to room temperature and concentrated in vacuo to remove ethanol and water. The residue was again taken in ethanol (12.5 L) and heated at reflux for 1 h and concentrated. This process of reflux and concentration with ethanol was repeated two more times (9.5 L and 5 L). TLC analysis in CMA-80 (chloroform 80%, methanol 18% and conc. NH$_4$OH 2%) showed complete hydrolysis of borate complex. To the residue obtained was added isopropanol (8 L) and heated at gentle reflux for 15 mins and cooled to 5° C. for 1 h. The solid was collected by filtration and recrystallized by dissolving in water (650 mL) and isopropanol (1.3 L) upon heating. The hot solution was diluted with isopropanol (11.6 L), heated at reflux for 15 min and cooled to 5° C. for 1 h. The solid obtained was collected by filtration and washed with isopropanol (250 mL) to furnish 670 g (58%) of the desired (2S,3R,4R,5R)-2-(4-aminofuro[3,2-d]pyrimidin-7-yl)-5-(hydroxymethyl)-3-methyl-tetrahydrofuran-3,4-diol hydrochloride as a white solid. $^1$HNMR (DMSO-d$_6$): δ 9.24 (bs, 2 H), 8.65 (s, 1H), 8.49 (s, 1 H), 5.03 (s, 1 H), 3.83-3.77 (m, 2 H), 3.70-3.65 (m, 2 H), 0.91 (s, 1 H); MS (ES$^+$): 282.39(100% M$^+$); HPLC purity 99.8%. [α]=+6.18 [c 1.65, H$_2$O]. Analysis: Calc. for $C_{12}H_{15}N_3O_5$·HCl·H$_2$O: C, 42.97; H, 5.41; N, 12.53; Cl, 10.44; Found: C, 43.04; H, 5.46; N, 12.33; Cl, 10.69.

The invention claimed is:

1. A method for the preparation of the β isomer of a 9-deazapurine derivative, which comprises forming a 9-deazapurine base on a 2-C-methyl-ribose protected with protecting groups at the 2- and 3-hydroxyl groups, and removing the protecting groups, wherein the protecting groups are benzyl groups, which comprises the step of preparing a compound of formula (2-4):

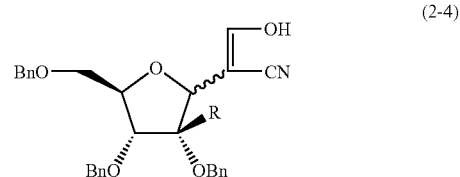

(2-4)

in which Bn represents a benzyl protecting group, and R represents a methyl group from a compound of formula (1-3):

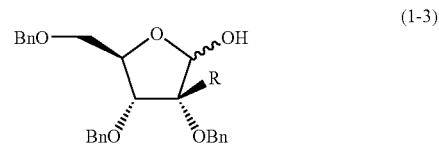

(1-3)

in which Bn represents a benzyl protecting group, and R represents a methyl group.

2. The method of claim 1, wherein the compound of formula (1-3) has been obtained by benzylation of 2-C-methyl-ribonolactone using benzyl bromide and sodium hydride as a base.

3. The method of claim 1 or 2, in which the β isomer of the 9-deazapurine derivative is selected from:
- (2S,3R,4R,5R)-2-(4-amino-5H-pyrrolo[3,2-d]pyrimidin-7-yl)-5-(hydroxymethyl)-3-methyl-tetrahydrofuran-3,4-diol;
- 7-((2S,3R,4R,5R)-3,4-dihydroxy-5-(hydroxymethyl)-3-methyl-tetrahydrofuran-2-yl)-3H-pyrrolo[3,2-d]pyrimidin-4(5H)-one;
- 2-amino-7-((2S,3R,4R,5R)-3,4-dihydroxy-5-(hydroxymethyl)-3-methyl-tetrahydrofuran-2-yl)-3H-pyrrolo[3,2-d]pyrimidin-4(5H)-one;
- (2S,3R,4R,5R)-2-(4-aminothieno[3,2-d]pyrimidin-7-yl)-5-(hydroxymethyl)-3-methyl-tetrahydrofuran-3,4-diol;
- 7-((2S,3R,4R,5R)-3,4-dihydroxy-5-(hydroxymethyl)-3-methyl-tetrahydrofuran-2-yl)thieno[3,2-d]pyrimidin-4(3H)-one;
- 2-amino-7-((2S,3R,4R,5R)-3,4-dihydroxy-5-(hydroxymethyl)-3-methyl-tetrahydrofuran-2-yl)thieno[3,2-d]pyrimidin-4(3H)-one;
- (2S,3R,4R,5R)-2-(4-aminofuro[3,2-d]pyrimidin-7-yl)-5-(hydroxymethyl)-3-methyl-tetrahydrofuran-3,4-diol;
- 7-((2S,3R,4R,5R)-3,4-dihydroxy-5-(hydroxymethyl)-3-methyl-tetrahydrofuran-2-yl)furo[3,2-d]pyrimidin-4(3H)-one;
- 2-amino-7-((2S,3R,4R,5R)-3,4-dihydroxy-5-(hydroxymethyl)-3-methyl-tetrahydrofuran-2-yl)furo[3,2-d]pyrimidin-4(3H)-one;
- (2S,3R,4R,5R)-2-(4-aminopyrazolo[1,5-a][1,3,5]triazin-8-yl)-5-(hydroxymethyl)-3-methyl-tetrahydrofuran-3,4-diol;

and pharmaceutically acceptable salts thereof.

4. The method of claim 3, in which the β isomer 9-deazapurine derivative is (2S,3R,4R,5R)-2-(4-aminofuro[3,2-d]pyrimidin-7-yl)-5-(hydroxymethyl)-3-methyl-tetrahydrofuran-3,4-diol, or a pharmaceutically acceptable salt thereof.

5. A compound of formula (2-4):

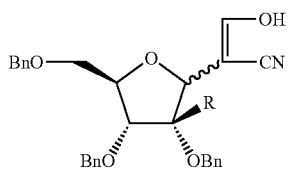

(2-4)

in which Bn represents a benzyl protecting group, and R represents a methyl group.

6. A compound of formula (6-3)

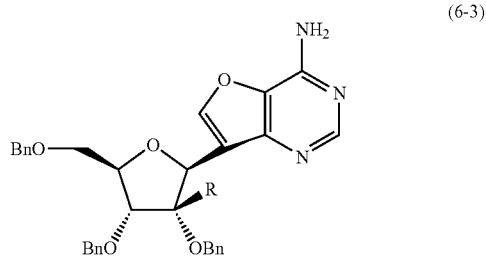

(6-3)

in which Bn represents a benzyl protecting group, and R represents a methyl group.

* * * * *